United States Patent [19]

Stockmeyer

[11] Patent Number: 4,606,222
[45] Date of Patent: Aug. 19, 1986

[54] EXTERNAL ENERGYLESS SAMPLE FOR DETERMINING THE CONTENT OF DISSOCIABLE POLAR LIQUIDS

[75] Inventor: Rolf Stockmeyer, Linnich-Tetz, Fed. Rep. of Germany

[73] Assignee: Kernforschungsanlage Julich, Fed. Rep. of Germany

[21] Appl. No.: 519,553

[22] Filed: Aug. 2, 1983

[30] Foreign Application Priority Data

Aug. 17, 1982 [DE] Fed. Rep. of Germany ....... 3230507

[51] Int. Cl.$^4$ ............................................. G01N 13/00
[52] U.S. Cl. ...................................... 73/73; 73/336.5; 204/430; 204/1 T
[58] Field of Search ...................... 73/73, 74, 335, 336, 73/336.5; 338/34, 35; 429/8, 118, 44, 241; 204/430, 1 W

[56] References Cited

U.S. PATENT DOCUMENTS

| | | | |
|---|---|---|---|
| 2,681,571 | 6/1954 | Becker | 73/73 |
| 2,800,521 | 7/1957 | Olcott et al. | 429/241 |
| 2,976,728 | 3/1961 | Brogan et al. | 73/336.5 |
| 3,458,845 | 7/1969 | Thoma | 73/336.5 |
| 3,523,244 | 8/1970 | Goodman et al. | 73/336.5 |
| 3,782,179 | 1/1974 | Richards | 73/73 |
| 3,857,284 | 12/1974 | Carron et al. | 73/336.5 |
| 4,369,104 | 1/1983 | Beckley | 429/44 |

FOREIGN PATENT DOCUMENTS 0160003 12/1981 Japan ..................................... 73/73

Primary Examiner—Charles Frankfort
Assistant Examiner—Patrick R. Scanlon
Attorney, Agent, or Firm—Scully, Scott, Murphy & Presser

[57] ABSTRACT

A process for the formation of a sample which does not require any external energy for determining the content of dissociable polar liquids in gases, expanded bodies, pouring charges of granular material, or electrically non-conductive liquids. The invention further relates to the provision of a sample probe which does not require external energy and which is applicable to the implementation of the process. A powder having a grain size in the range of between about 0.001 to 1 mm of an electrically deformable material having a crystalline or amorphic structure with at least a partial ionic bond and a specific resistance of at least $10^5$ Ohm/cm is compressed between two electrodes under a pressure of at least 100 bar, and continually maintained under pressure, whereby at least a portion of the components maintaining the powder under pressure is permeable to the moisture encompassing the sample.

12 Claims, 7 Drawing Figures

EXTERNAL ENERGYLESS SAMPLE FOR DETERMINING THE CONTENT OF DISSOCIABLE POLAR LIQUIDS

BACKGROUND OF THE INVENTION

1. Field of the Invention

The present invention relates to a process for the formation of a sample which does not require any external energy for determining the content of dissociable polar liquids in gases, expanded bodies, pouring charges of granular material, or electrically non-conductive liquids. The invention further relates to the provision of a sample or specimen which does not require external energy and which is applicable to the implementation of the process.

In drying processes, for the progression thereof, in addition to the temperature in the goods being dried and the pressure reigning in the goods, a role is also played by the concentration of the liquid (for example, water, alcohol, acetone) and the degree of concentration thereof. In order to be able to optimize the drying process with a view towards obtaining a saving in useable work through a variation in the temperature and of the pressure profile, it is desirable to have available a sample which facilitates the tracking and measuring of the concentration of the liquid.

A further area of utility of a sample for the measurement of a liquid content relates to the change in the water content in the ground, in connection with questions which are of energy-related commercial importance.

Water movements in the ground are of significance in multiple aspects with regard to energy systems. Consequently, it is desirable to be able to continually measure them in situ. During coal mining (in particular strip mining) the ground water is pumped off to a large extent, and there are diverging opinions with respect to the consequences. However, no measurements are available which indicate to which extent there is affected the moisture within the earth, for example, at the depth of tree roots or below buildings; for instance, as to how extensively the influence of weather conditions is still dominant over the ground moisture. Herein, this relates to water concentrations which allow the mineral strata (loam) to swell and shrink, and to minute water vapor densities in the ground, which are important to vegetation during the dry seasons.

Another area of utility of a sample for the measurement of the water content relates to the use of the ground as a heat storage. Heat transport and water transport are coupled with each other. Physical-mathematical models for ground heat storage and ground heat pumps accordingly require, for their experimental verification, a simple, continual in situ measuring method for the moisture.

In the sphere of nuclear energy use, there is encountered the problem of prognosticizing the heat transport processes across geological mineral deposits. The heating of the sediment strata across mineral deposits reduces the water content. Thereby, the heat conductivity reduces and, as a consequence thereof, the temperature gradient rises further. The measurement of the water content is thereby desirable also in this instance.

2. Discussion of the Prior Art

Methods for the measurement of the water content are presently known. Thus, it is known to withdraw samples from the goods being dried, and to determine the liquid content through weighing, or through more complex methods, such as light spectroscopy, neutron spectroscopy, or microwave absorption.

For continual in situ measurements, in principle, as samples there can be utilized open condensers, whose capacitance and loss factor depend upon the water content and upon the temperature of the dielectric medium through its dielectric function $\epsilon(\omega) = \epsilon' + \epsilon''$. The utilization of samples of that type, however, is quite demanding from the standpoint of the measurement technology, and can be employed only for small distances (approximately 1 meter) between the sample and the capacitance measuring bridge.

SUMMARY OF THE INVENTION

Accordingly, it is an object of the present invention to develop a process for the formation of a sample, as well as an inventive sample, which is adapted to be utilized for the determination of the content of the dissociable polar liquids and for continual measurements.

The foregoing object is achieved with regard to the formation of the sample through the intermediary of a process in which a powder having a grain size in the range of between about 0.001 to 1 mm of an elastically deformable material having a crystalline or amorphous structure with at least a partial ionic bond and a specific resistance of at least $10^5$ Ohm/cm is compressed between two electrodes under a pressure of at least 100 bar, and continually maintained under pressure, whereby at least a portion of the components maintaining the powder under pressure is permeable to the moisture encompassing the sample.

The compression of the powder can be effected manually (for example, by means of one or more screws pressing two pressure plates together) or through the action of a machine whereby, with respect to the pressure which is to be employed, this depends only upon the final pressure which is sought for the sample and which is to be continually maintained.

Since the final pressure depends upon the design of the components which take up the pressure, this should be so that there can be maintained a pressure in the sample of at least 100 bar. Hereby, it is to be naturally understood that as a powder which will take up the pressure, only such a powder comes into consideration which will elastically deform under the pressure which is to be applied and which will not evince a flow behavior.

Suitably, as materials which are to be placed under pressure, there can be employed $Al_2O_3$, $SiO_2$, stratified silicates (loam, pure clay), alumino silicates having a crystalline structure (zeolite), NaCl, MgO or ZnO.

As has evidenced itself, the thus formed samples provide an electrical output which depends upon the adsorption or, respectively, desorption of polar molecules. During quasi-steady state operation, when the moisture is uniformly distributed in the vicinity of the sample, as well as within the sample material, this electrical output can serve as a measure over the content of polar liquids in the medium which is being investigated. Hereby, for the case in which there is to be measured the liquid content in a solid body or in a charge of a granular material, suitably there should be employed samples where the material subjected to pressure consists of the same material as the material of the medium being investigated. For the case in which the material of the sample differs from the medium being investigated, the samples must be calibrated so that, for example, the electrical output which is emitted by the sample is measured in dependence upon the liquid content of small samples of the medium which is to be investigated. The thusly calibrated samples can be inserted for in situ measurements into the medium which is to be investigated.

During non-steady state operation, when the moisture in the sample still changes, a quantitative indication is not possible, since the sample voltage will oscillate. These oscillations, however, then provide an indication over the currently encountered change in the moisture.

The object on which the invention is predicated is achieved through a sample which includes two oppositely arranged electrodes, and one or more components which in a pressure-tightly sealed manner includes at least one portion of the space present between the electrodes, as well as a powder within the space which is under pressure and which has a grain size in the range of between 0.001 and 1 mm, which is constituted of an elastically deformable material of crystalline or amorphic structure with an at least partial ionic bond and a specific resistance of at least $10^5$ Ohm/cm, whereby at least one electrode and/or at least a portion of the parts which enclose the space in a pressure-tight manner is permeable to the moisture encompassing the sample.

The permeability for the moisture can be achieved in that at least one of the electrodes is constituted of a porous, pressure-resistant and electrically conductive material. Accordingly, it can be purposeful that the electrode which is permeable to the moisture is produced from sintered metal, such as sintered steel, from a metal mesh, or from a ceramic body with a conductive layer superimposed thereon, such as an $Al_2O_3$ member with a superimposed porous metal layer or superimposed graphite foil.

Hereby it is advantageous that the electrodes and the components which pressure-tightly enclose the space between the electrodes be so dimensioned that the ratio of the surface to the volume of the enclosed space is as large as possible.

A suitable embodiment of the sample pursuant to the invention evidences a rod-like or tubularly constructed inner electrode, and a tubular outer electrode which encompasses the inner electrode, wherein the material under pressure is located between the electrodes. Hereby, the outer electrode suitably consists of a metal mesh which is encompassed by a graphite foil.

A further suitable embodiment of the sample pursuant to the invention is distinguished through two plate-like constructed electrodes, between which there is located the material which is subjected to the pressure. The electrodes can hereby be constructed disc-shaped. In this instance, an advantageous embodiment of the sample pursuant to the invention consists of in that the space provided between the electrodes for the material under pressure is sealed off through an O-ring which is located between the two electrode discs, and wherein the two electrode discs are placed under pressure by means of two pressure discs.

As the material for the plate-shaped electrodes there can be employed sintered CuBe metal.

The principle of the sample pursuant to the invention is now elucidated on the basis of the drawings as illustrated hereinbelow. Moreover, in the drawings there are diagrammatically illustrated different embodiments of the sample, as well as the sample voltage of different samples for different drying procedures, as well as, for example, during the take-up of water.

BRIEF DESCRIPTION OF THE DRAWINGS

Reference may now had to the accompanying drawings; in which.

DETAILED DESCRIPTION

Figure 1:
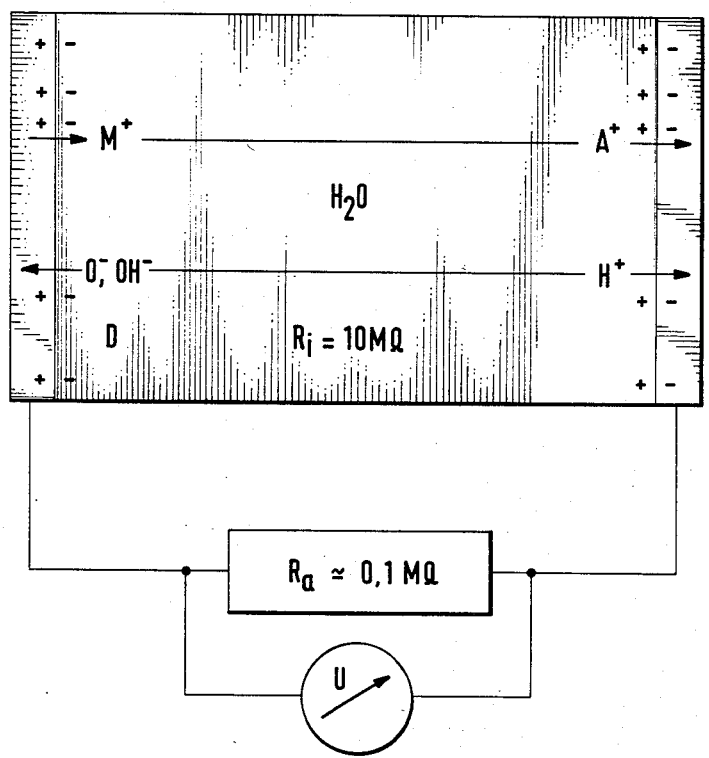
FIG. 1 is a diagrammatic representation of the principle of the inventive sample.

In FIG. 1 the material of the sample or specimen which is placed under pressure is identified by D (abbreviation for the dielectric medium), and the two electrodes by E. The internal resistance of the sample, for example, consists of $R_i = 10M$ Ohm.

Through the pressing in of the finely-granular, ion-evidencing dielectric medium there is produced a polarization, which builds up electrical surface fields on the right and left electrodes with opposite directions relative to the surface normals. On both boundary layers there is propagated a charge path for positive charge carriers from left to right and for negative charge carriers from right to left. In the dried condition of the material, short-term influenced charges flow through the larger current circuit, and the voltage U which is measured at $R_a$ drops off towards zero.

In the moist condition of the material, there flows a continuous current. The motive force is the equilibrium of chemical potentials.

As in electro-chemical cells, metal can go into solution on the left electrode, whereas an oxide layer will form on the right electrode. Added thereto are ion movements of the internal surface of the dielectric medium, which have the tendency to reduce the elastic and electrostatic energy accumulated during the pressing procedure. When, for example, these increase the water content in the dielectric material D, positive ions ($A^+$), as long as the micropores are still not filled with liquid, become more movable, whose charge is compensated through oxygen with a negative excess charge. Moreover, with an increase in the water content, there also increases the number of the movable $H^+$ and $OH^-$ ions. As a result, the electrical charge which is emitted by the sample rises just in that region in which the water content (or the content of other polar molecules which dissociate) is to be measured through the sample.

Samples or specimen can be built in with long inlet cables in larger formations in which there is to be measured the slow spatial-timewise change in the moisture. Extremely simple multimeters have an internal resistance of 0.1M Ohm; the insulation resistance of the usual cable is so large that the range of utilization of the sample is thereby not limited.

Figure 2:
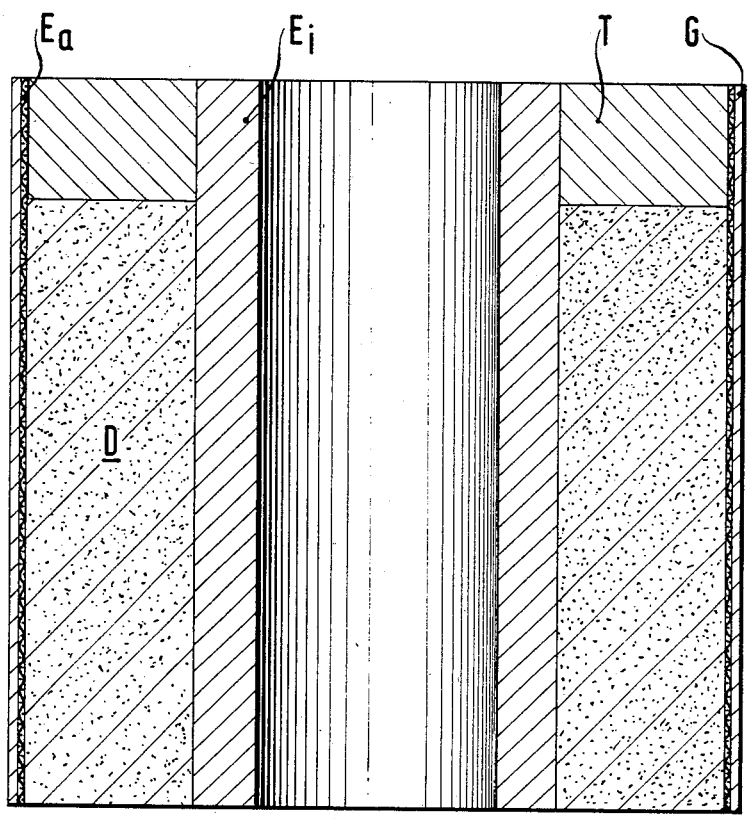
FIG. 2 is an illustration of a cylindrically formed sample with a tubular-shaped inner electrode.

The sample illustrated in FIG. 2 evidences a tubularly shaped inner electrode $E_i$ of brass, as well as an outer electrode $E_a$, which consists of a sieve mesh of stainless steel having a 0.1 mm thickness. (The terminals of the electrodes to which a measuring apparatus can be connected are not illustrated in the drawings.) In order to facilitate the compressing sequence, the electrode $E_a$ is encompassed by a graphite foil G as an external cylindrical mantle. Pressed in as the dielectric material D was zeolite NaX with a pressure of a few kbar. At the end surfaces, the pressure on the dielectric material was presently taken up by a ring T of insulating material; in the drawing only one ring is illustrated. The length and the diameter of the sample are 12 mm.

A sample or specimen of the type illustrated in FIG. 2 was experimentally built into a vacuum vessel, in conjunction with a temperature sensor Pt 100. Through valves connected to a vacuum pump and to a water container there could be adjusted the $H_2O$ gas pressure, which was indicated by a pressure measuring apparatus. The electrodes of the sample were connected with a 100 kOhm resistance, on which there was measured a voltage U(t) with a multimeter ($R_i = 10M$ Ohm). As was indicated, the slowly changing value $\overline{U}$ of the electrical voltage emitted by the sample determined over about 20 minutes, was taken as a quantitative indication with respect to the water content, in effect, after the completion of "actuating sequences" with the value U (t) slowly changing with the water content. Over a time span of two months there were tracked the adsorption and desorption cycles in order to determined the reproduceability of the emitted electrical output. When across the dried sample there is set a pressure increase from 2 mbar→P→15 mbar, there follows within 10 hours a voltage increase from 0→$\overline{U}$→24 mV. After a few days in equilibrium with the water supply the sample reached the voltage U=30 mV. At a pumping off of the $H_2O$, after 10 hours $\overline{U}$ drops to less than 1 mV.

Figure 3:
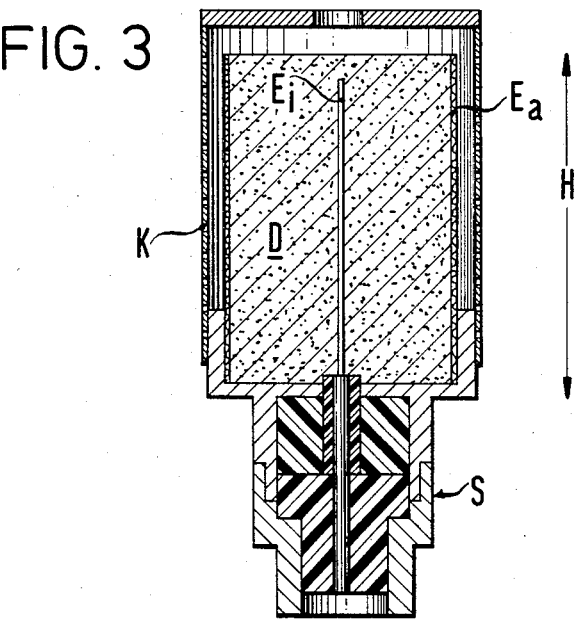
FIG. 3 illustrates a cylindrically formed sample with a wire-shaped inner electrode.

For the formation of a sample or specimen as illustrated in FIG. 3, zeolite NaX powder was filled into the interspace between the outer electrode $E_a$ consisting of a cylindrical wire mesh (mesh width 100μ, opening 44%), and the inner electrode $E_i$ consisting of a coaxial inner conductor (diameter=2mm) which is enveloped by a fine wire mesh of stainless steel.

The two electrodes $E_i$ and $E_a$ were retained at a distance to each other at one end by means of a coaxial sleeve. Through the action of a press, the powder was compressed. Prior to compression, the height of the filled in powder consisted of about 40 mm, after the compressing, in accordance with the pressure and filling density, approximately 10 to 30 mm. After the compressing sequence, the sample was provided with an outer protective grid K, the inner conductor soldered to the contact sleeve of a BNC coupling element, and a BNC sleeve was screwed on for connection of a coaxial cable.

Figure 4:
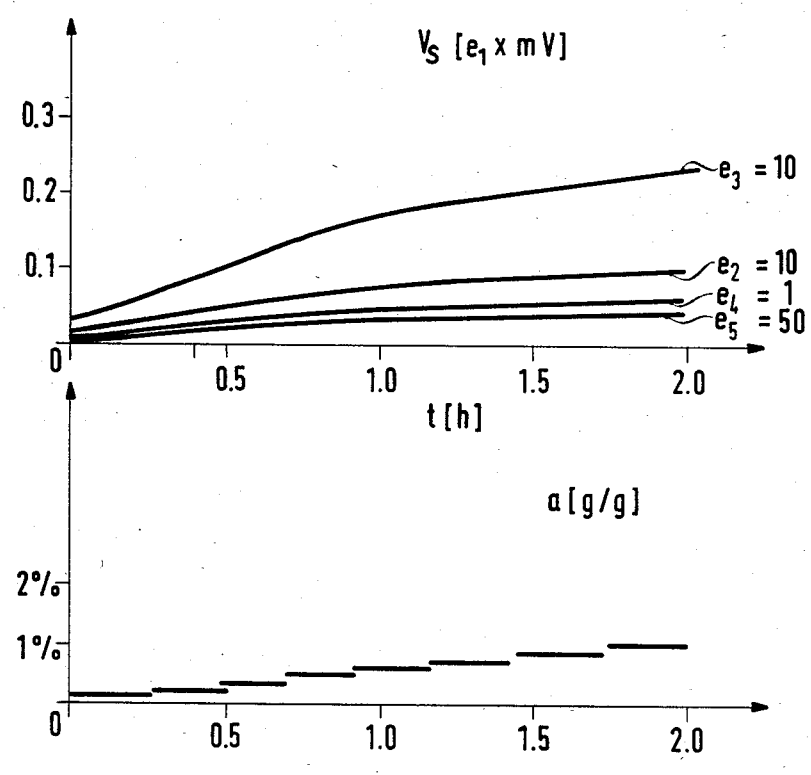
FIG. 4 is a measuring graph of the sample voltage during the water take-up of a zeolite block.
Figure 5:
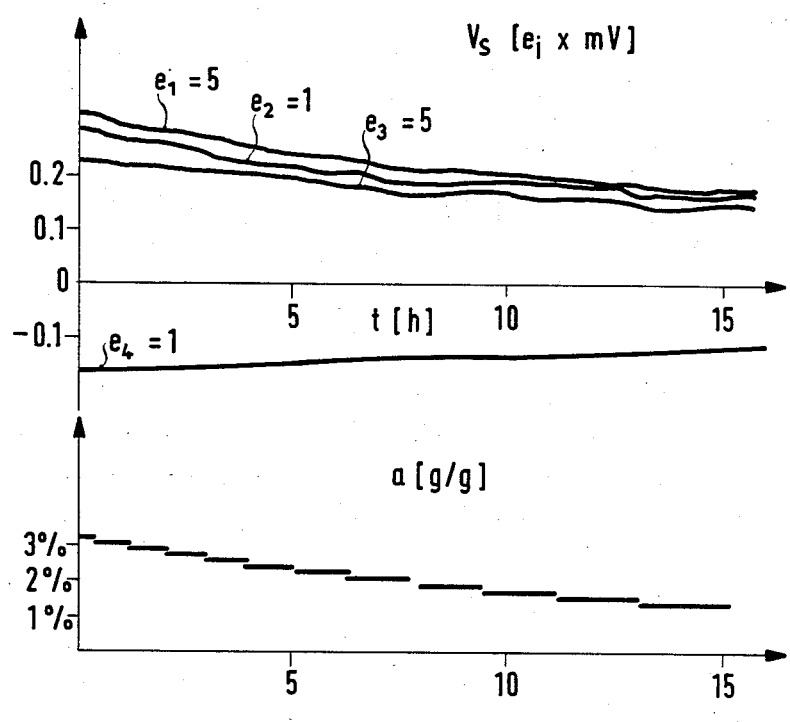
FIG. 5 is a measuring graph of the sample voltage during the drying of a zeolite block.

Measurements were effectuated with a series of samples of the type represented in FIG. 3, whose results are illustrated in FIGS. 4 and 5. A cylindrical zeolite block (850 cm³) cast from NaX mash was introduced into a housing together with four samples (as well as temperature sensor Pt 100), which was heatable and to be aerated. Moreover, through a filter cloth, with which the housing was equipped, water was introduced into the housing, so that the moisture in the zeolite block could be increased. The water content of the zeolite block was determined through continually effected weight determinations of the zeolite block.

The zeolite block and the samples were brought into a dried, steady-state condition wherein, for a period of one week, the housing temperature was maintained at $95° \leq T \leq 100°$ C., and the housing was aerated. The electrical output emitted by the samples hereby dropped down to extremely low values (pW). Water was then introduced into a supply container, from which it streamed through a thin tube to the filter cloth with which the housing was equipped. In FIG. 4 there is represented the plot of the water content as calculated from the weight of the zeolite block, as well as the concurrent plot of the sample voltages. Indicated on the graphs is the scale factor $e_1$ associated with the individual samples ($e_2$ through $e_5$), with which there are to be multiplied the values read off on the mV scale. For the most sensitive sample, the voltage change consisted of about 2 mV for each 1% water take-up.

In FIG. 5 there are represented the sample voltages which synchronously reduce with the water content in the range of below 3%, after oscillations at the beginning of the drying phase. The most sensitive sample ($e_5 = 5$) evidences in this range a voltage change of 1 mV per 1% water reduction.

Figure 6:
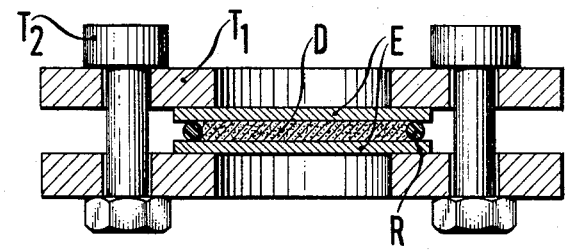
FIG. 6 illustrates a plate-shaped sample.

From FIG. 6 there can be further ascertained the schematic construction of a plate shaped sample. The electrodes E consists of disc-shaped plates of CuBe, which are maintained at a spacing through an O-ring R.

The two plates are maintained under pressure by means of two brass rings $T_1$ which are pressed together through screws $T_2$ constructed of Teflon, so as to place the zeolite NaX material in the space between the electrodes E and the O ring under pressure.

3.5 g of a readily vaporizable polar liquid (ethanol, acetone) was applied on one of the electrodes of the plate-shaped sample pursuant to FIG. 6. The electrical voltage between the electrodes was measured with a high-ohmic multimeter ($R_1 = 10M$ Ohm) whose input is, however, bridged with a load resistor $R_a = 10$ kOhm.

Figure 7:
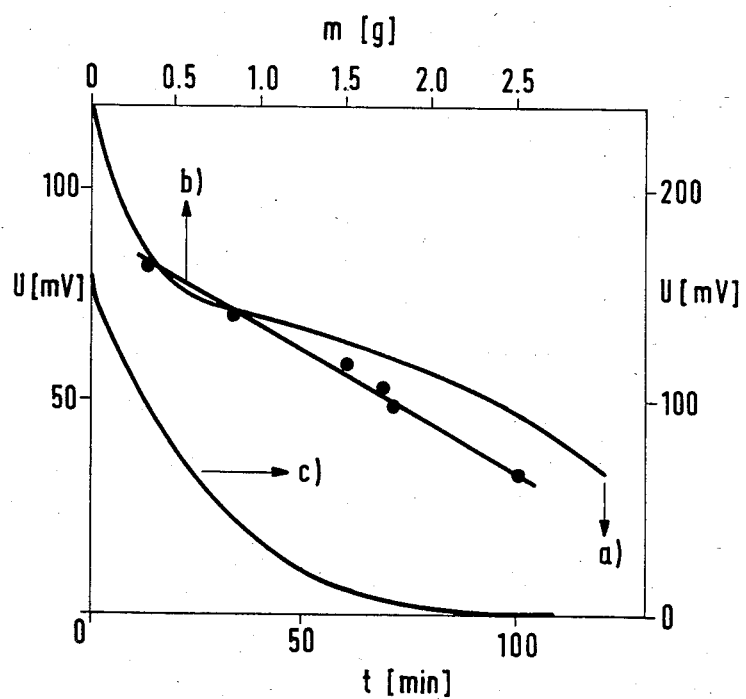
FIG. 7 is a measuring graph of the voltage of a plate-shaped sample with a 10 kOhm load resistance during drying in air at room temperature.

Upon vaporizing of the liquid, and consequent drying of the sample material, the sample voltage dropped off in a manner as illustrated in FIG. 7. Curve a illustrates the timewise plot of the voltage after moistening with ethanol (scales to the left and bottom). Curve b illustrates the interrelationship between the measured voltage and the content of ethanol in the sample. Curve c illustrates the timewise voltage plot after moistening the sample with acetone (scales to the right and bottom).

What is claimed is:

1. In a process for the formation of an external energy-less apparatus for the determination of the content of dissociable polar liquids in gases, expanded solid bodies, charges of granular material, or electrically non-conductive liquids; the improvement comprising: compressing powder having a grain size in the range of between 0.001 to 1 mm from an elastically deformable material of crystalline or amorphic structure with an at least partially ionic bond and a specific resistance of at least $10^5$ Ohm/cm between components including two electrodes under a pressure of at least about 100 bar; and continually maintaining the powder under pressure whereby said permanently maintained pressure elastically deforms said powder and upon adsorption and desorption of molecules of said polar liquid produces a continuous current dependent upon the amount of adsorption and desorption of molecules of said polar liquid within the gas, liquid or solid being tested thereby indicating the content of polar liquids therein, and whereby at least a portion of the components maintaining the powder under pressure is permeable to moisture encompassing the apparatus.

2. A process as claimed in claim 1, wherein the powder subjected to pressure is selected from the group consisting of $Al_2O_3$, $SiO_2$, silicate strata, such as loam, pure clay, crystalline alumino silicate, zeolite, NaCl, MgO and ZnO.

3. An apparatus for the determination of the content of dissociable polar liquids in gases, expanded solid bodies, charges of granular material, or electrically non-conductive liquids, wherein said apparatus does not require external energy; comprising two oppositely spaced electrodes defining a space therebetween, at least one component pressure-tightly enclosing at least a portion of the space intermediate the electrodes; and a powder within the space subjected to pressure, said component permanently maintaining said powder under pressure, said powder having a grain size in the range of between 0.001 and 1 mm, consituted of an elastically deformable material of crystalline or amorphic structure with an at least partial ionic bond and a specific resistance of at least $10^5$ Ohm/cm, wherein at least one electrode and at least a portion of the component pressure-tightly enclosing said sapce is permeable to moisture encompassing the apparatus, whereby said permanently maintained pressure elastically deforms said powder and upon adsorption and desorption of molecules of said polar liquid produces a continuous current dependent upon the amount of adsorption and desorption of molecules of said polar liquid within the gas, liquid or solid being tested thereby indicating the content of polar liquids therein.

4. An apparatus as claimed in claim 3, wherein at least one of said electrodes is constituted of a porous, pressure-resistant and electrically conductive material.

5. An apparatus as claimed in claim 4, wherein the electrode which is permeable to moisture is constituted of sintered metal, such as sintered steel, a metal mesh, or a ceramic member with a conductive layer superimposed thereon, such as an $Al_2O_3$ member having a porous metal layer or graphite foil superimposed thereon.

6. An apparatus as claimed in claim 3, wherein the electrodes and the components pressure-tightly enclosing the space between the electrodes are dimensioned so as to maximize the ratio of the surface area of the space normal to the electrodes and the volume of the enclosed space.

7. An apparatus as claimed in claim 3, including a rod-like or tubular inner electrode; and an outer electrode encompassing the inner electrode, the material subjected to pressure being arranged between the electrodes.

8. An apparatus as claimed in claim 7, wherein the outer electrode consists of a metal mesh encompassed by a graphite foil.

9. An apparatus as claimed in claim 3, including two plate shaped electrodes, the material subjected to pressure being arranged between the electrodes.

10. An apparatus as claimed in claim 9, wherein the electrodes are disc-shaped.

11. An apparatus as claimed in claim 10, comprising an O-ring between the two electrode discs for pressure-tightly sealing the space containing the material subjected to pressure; and including two pressure discs for imparting pressure to the two electrode discs.

12. An apparatus as claimed in claim 9, wherein the plate shaped electrodes are constituted of sintered CuBe metal.

* * * * *